United States Patent
Nissan et al.

(10) Patent No.: US 8,771,220 B2
(45) Date of Patent: Jul. 8, 2014

(54) GLAUCOMA ACTIVE PRESSURE REGULATION SHUNT

(75) Inventors: Oded M. Nissan, Modiin (IL); Oshrit Hertz, Modiin (IL)

(73) Assignee: Alcon Research, Ltd., Fort Worth, TX (US)

(*) Notice: Subject to any disclaimer, the term of this patent is extended or adjusted under 35 U.S.C. 154(b) by 184 days.

(21) Appl. No.: 13/313,193

(22) Filed: Dec. 7, 2011

(65) Prior Publication Data

US 2013/0150773 A1   Jun. 13, 2013

(51) Int. Cl.
*A61M 5/00* (2006.01)

(52) U.S. Cl.
USPC ................................. 604/9; 604/8

(58) Field of Classification Search
USPC ............. 604/8–10, 264–266, 294, 298, 521; 606/4–6, 107, 153; 623/4.1, 6.64, 623/23.68
See application file for complete search history.

(56) References Cited

U.S. PATENT DOCUMENTS

| | | | |
|---|---|---|---|
| 5,370,607 A * | 12/1994 | Memmen | 604/8 |
| 5,558,629 A | 9/1996 | Baerveldt et al. | |
| 5,626,559 A * | 5/1997 | Solomon | 604/9 |
| 5,882,327 A | 3/1999 | Jacob | |
| 6,050,970 A | 4/2000 | Baerveldt et al. | |
| 6,261,256 B1 | 7/2001 | Ahmed | |
| 6,510,600 B2 | 1/2003 | Yaron | |
| 7,025,740 B2 | 4/2006 | Ahmed | |
| 7,195,608 B2 * | 3/2007 | Burnett | 604/9 |
| 7,670,310 B2 | 3/2010 | Yaron | |
| 7,811,268 B2 * | 10/2010 | Maldon Ado Bas | 604/294 |
| 7,862,531 B2 * | 1/2011 | Yaron et al. | 604/8 |
| 8,394,048 B2 * | 3/2013 | Burnett | 604/9 |
| 2003/0093084 A1 | 5/2003 | Nissan et al. | |
| 2003/0229303 A1 | 12/2003 | Haffner et al. | |
| 2005/0250788 A1 | 11/2005 | Tu et al. | |
| 2005/0288617 A1 * | 12/2005 | Yaron et al. | 604/8 |
| 2006/0036208 A1 * | 2/2006 | Burnett | 604/9 |
| 2006/0173397 A1 | 8/2006 | Tu et al. | |
| 2006/0189916 A1 * | 8/2006 | Bas | 604/8 |
| 2007/0078371 A1 | 4/2007 | Brown et al. | |
| 2008/0154173 A1 * | 6/2008 | Burnett | 604/9 |
| 2009/0177138 A1 * | 7/2009 | Brown et al. | 604/8 |
| 2009/0204053 A1 | 8/2009 | Nissan et al. | |
| 2010/0004635 A1 | 1/2010 | Lin et al. | |
| 2010/0114006 A1 | 5/2010 | Baerveldt et al. | |
| 2010/0185138 A1 | 7/2010 | Yaron et al. | |
| 2010/0274259 A1 | 10/2010 | Yaron et al. | |
| 2010/0331975 A1 | 12/2010 | Nissan et al. | |
| 2011/0071456 A1 | 3/2011 | Rickard | |
| 2011/0077626 A1 | 3/2011 | Baerveldt et al. | |

* cited by examiner

*Primary Examiner* — Jackie Ho
*Assistant Examiner* — Mark K Han

(57) ABSTRACT

In various embodiments, a glaucoma shunt may include a tube having an anterior portion (with an opening) and a posterior portion. The glaucoma shunt may include a valve, inside the tube, coupled to a drainage portion. The tube may be configured to couple to a first portion of an eye and the drainage portion may be configured to couple to a second portion of the eye. In some embodiments, the drainage portion may be configured to move the valve relative to the tube such that when the eye expands, the valve moves away from the opening in the anterior portion of the tube to increase fluid flow. The drainage portion may further be configured to move the valve relative to the tube such that when the eye contracts, the valve moves toward the opening in the anterior portion of the tube to decrease fluid flow.

17 Claims, 5 Drawing Sheets

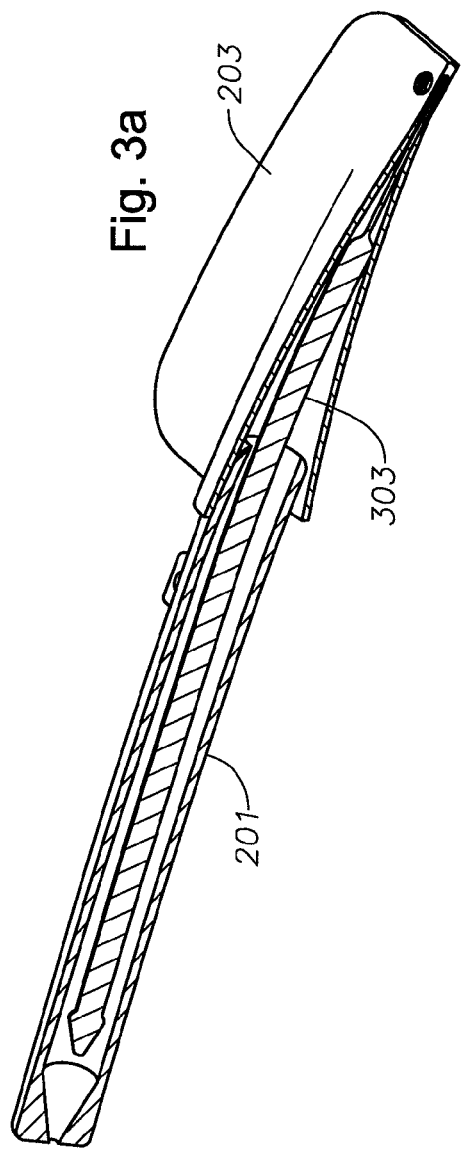
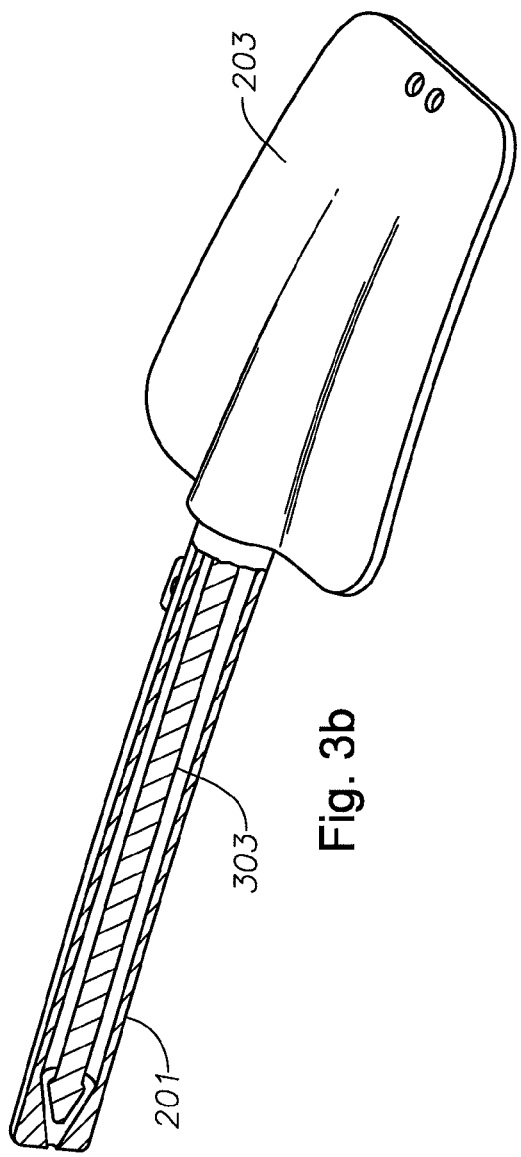

GLAUCOMA ACTIVE PRESSURE REGULATION SHUNT

FIELD OF THE INVENTION

The present invention generally pertains to glaucoma treatment. More particularly, but not by way of limitation, the present invention pertains to a intraocular pressure regulation.

DESCRIPTION OF THE RELATED ART

Glaucoma, a group of eye diseases affecting the retina and optic nerve, is one of the leading causes of blindness worldwide. Glaucoma results when the intraocular pressure (IOP) increases to pressures above normal for prolonged periods of time. IOP can increase due to an imbalance of the production of aqueous humor and the drainage of the aqueous humor. Left untreated, an elevated IOP causes irreversible damage the optic nerve and retinal fibers resulting in a progressive, permanent loss of vision.

The eye's ciliary body epithelium constantly produces aqueous humor, the clear fluid that fills the anterior chamber of the eye (the space between the cornea and iris). The aqueous humor flows out of the anterior chamber through the uveoscleral pathways, a complex drainage system. The delicate balance between the production and drainage of aqueous humor determines the eye's IOP.

Open angle (also called chronic open angle or primary open angle) is the most common type of glaucoma. With this type, even though the anterior structures of the eye appear normal, aqueous fluid builds within the anterior chamber, causing the IOP to become elevated. Left untreated, this may result in permanent damage of the optic nerve and retina. Eye drops are generally prescribed to lower the eye pressure. In some cases, surgery is performed if the IOP cannot be adequately controlled with medical therapy.

Acute angle closure glaucoma is less prevalent. Acute angle closure occurs because of an abnormality of the structures in the front of the eye. In most of these cases, the space between the iris and cornea is more narrow than normal, leaving a smaller channel for the aqueous to pass through. If the flow of aqueous becomes completely blocked, the IOP rises sharply, causing a sudden angle closure attack.

Secondary glaucoma occurs as a result of another disease or problem within the eye such as: inflammation, trauma, previous surgery, diabetes, tumor, and certain medications. For this type, both the glaucoma and the underlying problem must be treated.

FIG. 1 is a diagram of the front portion of an eye that helps to explain the processes of glaucoma. In FIG. 1, representations of the lens 110, cornea 120, iris 130, sclera 190, choroid 195, ciliary bodies 140, trabecular meshwork 150, and Schlemm's canal 160 are pictured. Anatomically, the anterior chamber 170 of the eye includes the structures that cause glaucoma. Aqueous fluid is produced by the ciliary bodies 140 that lie beneath the iris 130 and adjacent to the lens 110 in the anterior chamber 170. This aqueous humor washes over the lens 110 and iris 130 and flows to the drainage system located in the angle of the anterior chamber 170. The angle of the anterior chamber 170, which extends circumferentially around the eye, contains structures that allow the aqueous humor to drain. The first structure, and the one most commonly implicated in glaucoma, is the trabecular meshwork 150. The trabecular meshwork 150 extends circumferentially around the anterior chamber 170 in the angle. The trabecular meshwork 150 seems to act as a filter, limiting the outflow of aqueous humor and providing a back pressure producing the IOP. Schlemm's canal 160 is located beyond the trabecular meshwork 150. Schlemm's canal 160 has collector channels that allow aqueous humor to flow out of the anterior chamber 170. The two arrows in the anterior chamber 170 of FIG. 1 show the flow of aqueous humor from the ciliary bodies 140, over the lens 110, over the iris 130, through the trabecular meshwork 150, and into Schlemm's canal 160 and its collector channels.

SUMMARY

In various embodiments, a glaucoma shunt may include a tube having an anterior portion (with an opening) and a posterior portion. The glaucoma shunt may include a valve, inside the tube, coupled to a drainage portion. The tube may be configured to couple (e.g., through suture holes) to a first portion of an eye and the drainage portion may be configured to couple (e.g., through suture holes) to a second portion of the eye. In some embodiments, the drainage portion may be configured to move the valve relative to the tube such that when the eye expands, the valve moves away from the opening in the anterior portion of the tube to increase fluid flow through the opening. The drainage portion may further be configured to move the valve relative to the tube such that when the eye contracts, the valve moves toward the opening in the anterior portion of the tube to decrease fluid flow through the opening. In some embodiments, the drainage portion may include a C-Matrix pocket made of nano fiber non-woven polymeric material. The valve may be arrow-shaped and may move inside an arrowed shaped tube interior such that as the arrow-shaped valve moves toward/away from the arrow-shaped interior volume, the sides of the arrow shaped valve may approach the interior sides of the tube to decrease/increase a size of an opening into the tube. In some embodiments, the valve may be coupled to the drainage portion through a flat back plate. In some embodiments, the drainage portion may be configured to at least partially slide over the posterior portion of the tube.

BRIEF DESCRIPTION OF THE DRAWINGS

For a more complete understanding of the present invention, reference is made to the following description taken in conjunction with the accompanying drawings in which:

FIGS. 3a-b illustrate a cross section of FIG. 2, with the valve in a fully open (FIG. 3a) and partially open (FIG. 3b) position, according to an embodiment.

It is to be understood that both the foregoing general description and the following detailed description are exemplary and explanatory only and are intended to provide a further explanation of the present invention as claimed.

DETAILED DESCRIPTION OF THE EMBODIMENTS

In various embodiments, a glaucoma shunt 200 may be provided to actively regulate intraocular pressure (IOP) in glaucoma patients. As an active implant, the shunt 200 may provide pressure control over time, prevent post-operation symptoms such as hypotony, and may adapt to variable conditions between patients.

Figure 1:
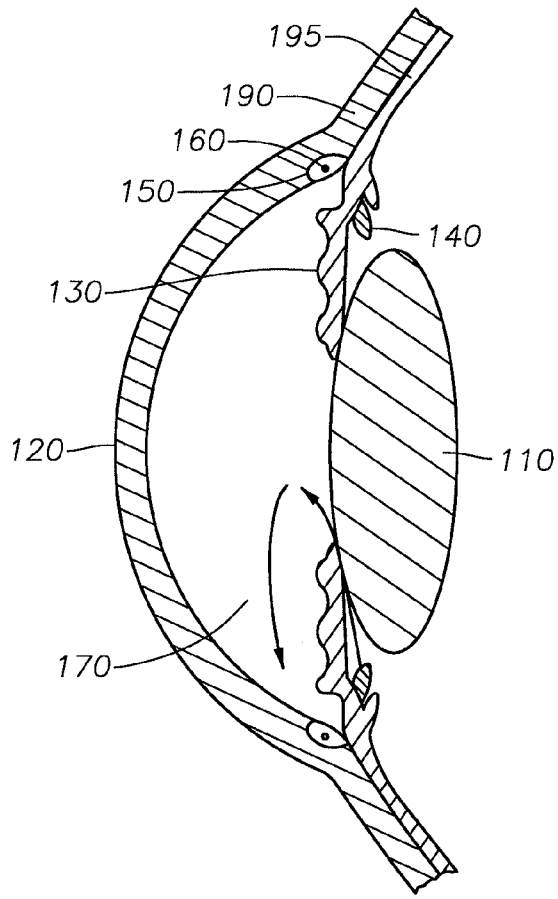
FIG. 1 illustrates a view of the eye.
Figure 2:
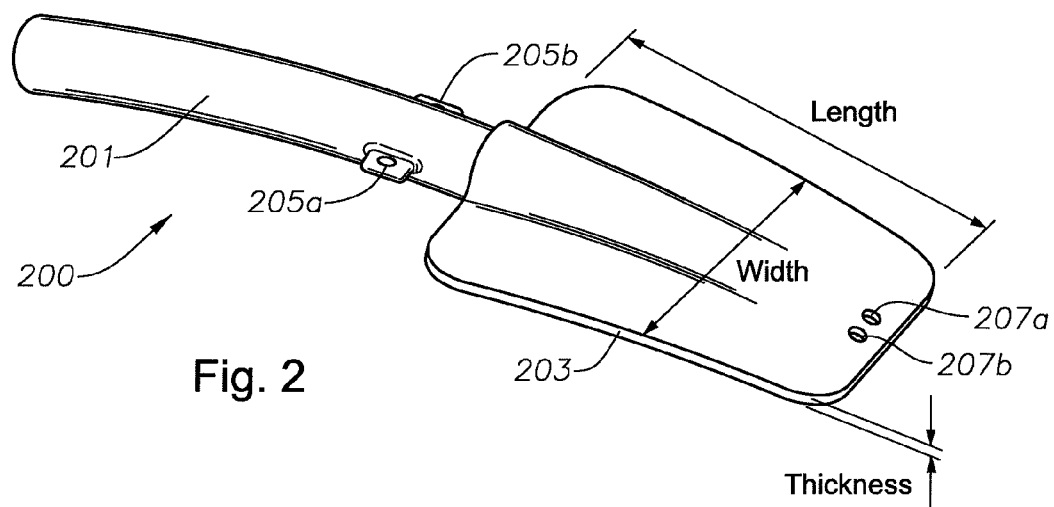
FIG. 2 illustrates a shunt comprising a tube and drainage portion, according to an embodiment.
Figure 4:
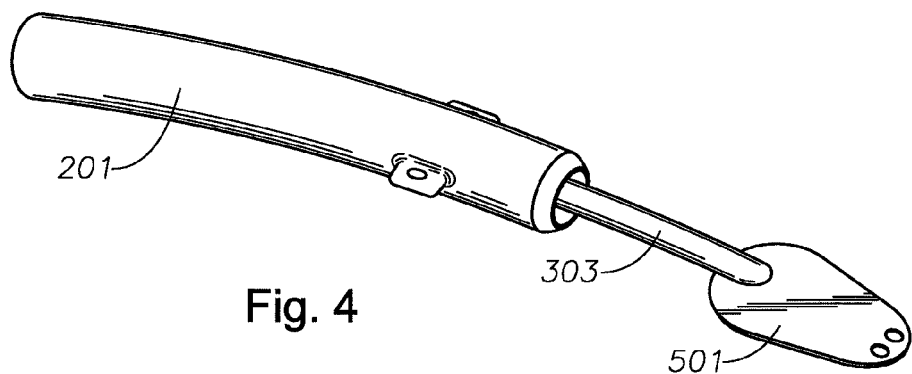
FIG. 4 illustrates a view with the pocket hidden, making the back-plate of the valve visible, according to an embodiment.

As seen in FIGS. 2 and 3a-b, the glaucoma shunt 200 may include at least three components: a tube 201, a valve 303 (e.g., see FIGS. 3a-b) and a drainage portion 203 (e.g., a C-Matrix pocket). An implanted shunt may provide a path for fluid flow (e.g., aqueous humor) out of the anterior chamber 170 of the eye and into, for example, the sclera 190 or suprachoroidal space (between the sclera 190 and choroid 195). The shunt 200 may be configured to open and close the valve 303, based on expansion and contraction of the eye globe associated with increases and decreases in intraocular pressure (IOP). As the valve 303 opens and closes fluid flow through the shunt may correspondingly increase and decrease. The tube 201 and valve body may have smooth surfaces and be made of a polymer or metal (e.g., a Nickel Titanium (NiTi) alloy).

As seen in FIGS. 3a-b, the tube 201 may provide a path for fluid passage, and the valve 303 may control the flow through the tube 201 and into the drainage portion 203. As fluid is absorbed by the interior of the drainage portion 203, it may travel through the drainage portion 203 and to the exterior of the drainage portion 203. In some embodiments, the drainage portion 203 may include a C-Matrix pocket that may include nano fiber non-woven polymeric material (e.g., fluoropolymer such as polyvinylidene difluoride (PVDF) or a copolymer of polylactic acid and polyglycolic acid (PLGA)) Other materials may also be used (e.g., other polymers or biocompatible ceramic or metal fibers). The fibers may be biodegradable. The fibers may be biostable. In some embodiments, the C-Matrix pocket may have fibers with void spaces between the fibers that are sized to allow flow of aqueous humor through the C-matrix pocket while inhibiting cell and tissue growth (e.g., scar tissue formation) on the C-Matrix pocket. In some embodiments, the fibers of the C-Matrix pocket may have a thickness of between approximately 10 nanometers and approximately 100,000 nanometers (e.g., in one embodiment, between approximately 3000-5000 nanometers). Other thicknesses are also possible. The drainage portion 203 may have an enlarged surface area (e.g., through the wing-shaped extensions as seen in FIG. 2) to increase the effective surface area for distributing and filtering the fluid. In some embodiments, the C-Matrix pocket may be between about 1 mm and about 15 mm along its longest dimension (length) and between about 1 mm and about 10 mm along its width (which may taper as shown in FIGS. 3a-b). The C-matrix pocket may have a thickness of between approximately 25 microns and about 150 microns. Other dimensions for the length, width, and thickness of the C-Matrix pocket are also contemplated. In some embodiments, the C-Matrix pocket may include a fiber matrix as described in U.S. Patent Publication No. 20100331975, entitled "Fiber Matrix For Maintaining Space in Soft Tissues" by Oded Nissan, Ira Yaron, and Jonathan Ben-Zvi, filed Jun. 25, 2010, which is hereby incorporated by reference in its entirety as though fully and completely set forth herein. The wing-shaped extensions may also increase the stability of the shunt 200 by inhibiting rolling on the surface of the eye globe (which may put stress on the sutures and/or the eye surface). In some embodiments, the corners of the C-Matrix pocket may be rounded. In some embodiments, the pressure of the aqueous humor flowing into the C-Matrix pocket, may cause the C-Matrix pocket to stretch and expand which may facilitate additional flow through the C-Matrix pocket. As the pressure of the aqueous humor falls, the C-Matrix pocket may contract (thus allowing less flow through the C-Matrix pocket). In some embodiments, the C-Matrix pocket shape may not stretch and contract. In some embodiments, the C-Matrix pocket may be coated with a biodegradable coating which may resist flow when the C-Matrix pocket is first implanted, however, through time, the coating may erode thus allowing increased flow through the C-Matrix pocket. The biodegradable coating may include a therapeutic agent (e.g., an anti-metabolite or antibiotic or glaucoma-treating drug). In some embodiments, the C-Matrix pocket may not be coated with a biodegradable coating.

Figure 5:
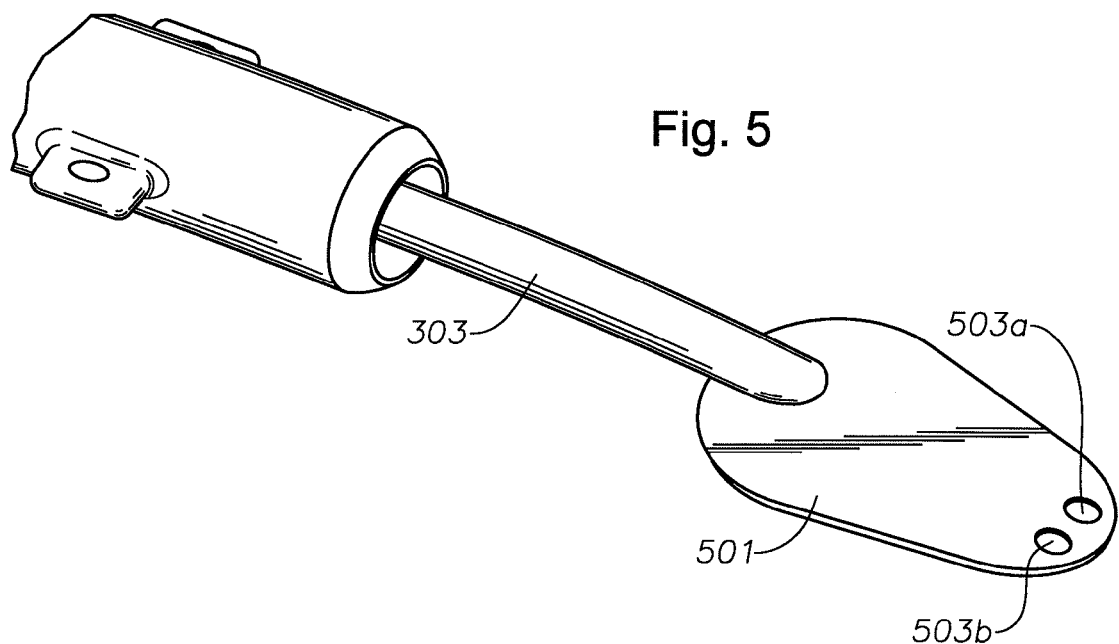
FIG. 5 illustrates an enlarged view of the valve back-plate and suture holes, according to an embodiment.

In some embodiments, the drainage portion 203 may include other components that may facilitate distribution of the fluid over an area of discharge. In some embodiments, the discharge portion 203 may include a tube opening without a distribution component. For example, a back plate 501 (as seen in FIG. 5) of the valve 303 may be sutured directly to the eye and the fluid may flow out of the tube 201 around the valve body 303.

Figure 8:
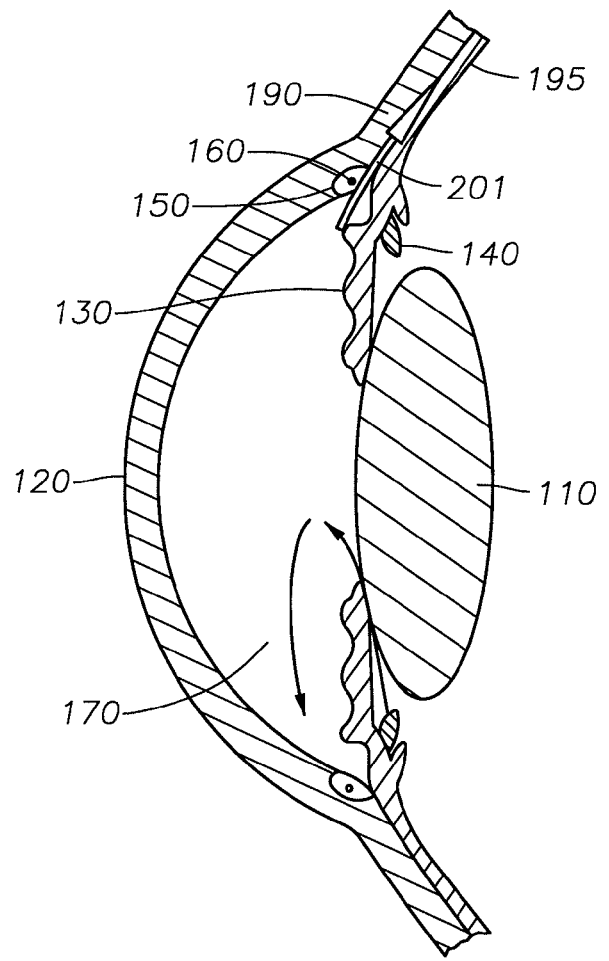
FIG. 8 illustrates the anterior portion of the tube located in the anterior chamber, according to an embodiment.

In some embodiments, an anterior portion of the tube 201 may be inserted into the anterior chamber 170 (e.g., as seen in FIG. 8) and a posterior portion of the tube 201 may be covered by the drainage portion 203. Once inserted into the eye, the tube 201 may be coupled (e.g., through suture holes 205a,b) to a portion of the eye inside the anterior chamber (e.g., the cornea, iris, ciliary muscle, etc.) and the drainage portion 203 may be coupled (e.g., through suture-holes 207a,b) to another portion (e.g., in the sclera 190 or the suprachoroidal space) of the eye. Other coupling mechanisms are also contemplated (e.g., grafts, adhesive, etc). While two suture holes 205a,b and 207a,b are shown, other numbers of suture-holes are also contemplated. As the eye globe expands and contracts, the tube 201 (coupled to one part of the eye) may move relative to the drainage portion 203 (coupled to another part of the eye).

Figure 6:
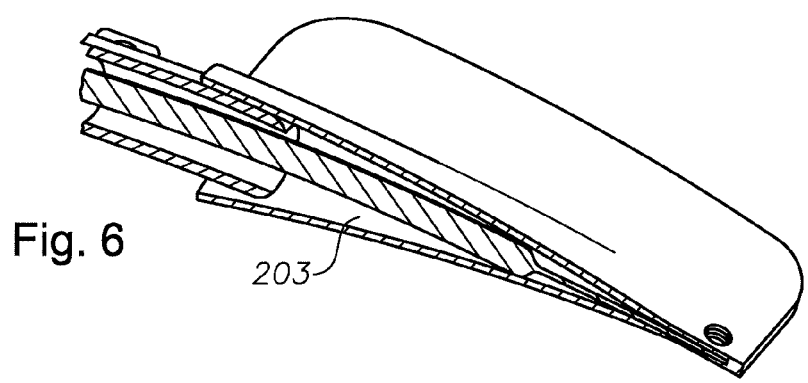
FIG. 6 illustrates an enlarged view of the cross section of the posterior part of the shunt, according to an embodiment.
Figure 7A:
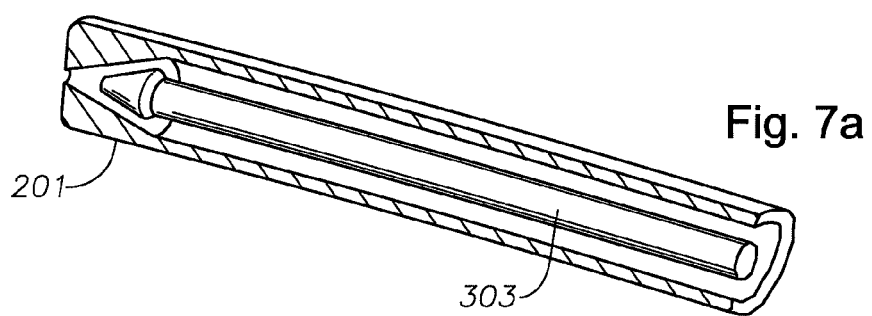
FIGS. 7a-b illustrate an enlarged view of two embodiments of the anterior part of the shunt, with the valve closer to the tube opening, limiting the fluid passage area.
Figure 7B:
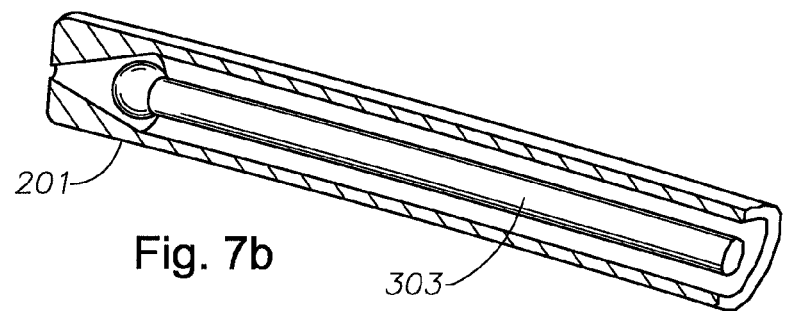

As seen in FIGS. 3a-b, the valve 303 inside the tube 201 may be shaped to allow fluid to flow through the tube opening and over the valve body when the valve body is pulled away from the tube opening. As seen in FIGS. 5 and 7a, the valve body may be arrow shaped. Other shapes are also contemplated (e.g., round (as seen in FIG. 7b), rectangular, etc). As further seen in FIG. 5, the valve 303 may be attached to a back plate 501 (which may be a flat back plate shaped to fit inside the drainage portion 203). The flat back plate 501 may include suture holes 503a,b that are aligned with suture holes 207a,b in the drainage portion 203 (e.g., the C-Matrix pocket seen in cross section in FIG. 6) such that the same sutures may anchor both suture holes 503a,b and 207a,b. In some embodiments, the flat back plate 501 may be attached to the drainage portion 203 through adhesive, a friction fit, etc. that may provide attachment between the flat back plate 501 instead of, or in addition to, the aligned suture holes 503a,b and 207a,b.

The interaction between the sutured flat back plate 501 and the sutured tube 201 may use eye global expansion (during IOP rise) and global contraction (during IOP fall) to move the valve 303 (as used herein, the "eye globe" includes the internal structures of the eye that expand with a rise in IOP). Since the tube 201 is anchored by its suture holes to one point on the eye globe, and the pocket and valve are anchored at a more posterior point on the eye globe, an increase in an eye globe radius causes the valve 303 to glide in an opposite direction from the tube 201 (e.g., see FIGS. 3a-b). The movement of the valve 303 away from the anterior portion of the tube 201 may provide a larger opening at the anterior portion of the tube 201 to allow increased fluid passage through the tube 201. Fluid passage out of the anterior chamber 170 and through the tube 201 may result in a lowering of pressure in the anterior chamber 170. The eye globe radius may consequently reduce in volume, leading to gliding of the valve 303 toward the anterior portion of the tube 201 resulting in a reduced tube opening size. As the opening's cross section area is reduced, the flow through the tube 201 may decrease. In some embodiments, fluid may flow between the tube 201 and the distal end of the valve (e.g., over the arrow or ball shape) and along the length of the tube 201. The tube 201 may also slide internally to the drainage portion 203 (e.g., as seen in FIGS. 3a-b, the drainage portion 203 may slide over the posterior portion of the tube 201 and may include a seal between the drainage portion 203 and the tube 201). The seal may include an o-ring or a tight fit between the drainage portion 203 and the tube/valve to inhibit fluid flow out of the tube 201 at the interface between the tube 201 and the drainage portion 203.

FIG. 8 illustrates an embodiment with the anterior portion of the tube 201 located in the anterior chamber 170. The C-Matrix pocket may cover the valve and the posterior portion of the tube 201 may be implanted in the sclera 190 or the suprachoroidal space (between the sclera 190 and choroid 195). Other implantation sites for the posterior portion of the tube 201 are also contemplated.

In some embodiments, depending on the application and the materials, geometry and arrangement of the fibers and the C-Matrix pocket, the C-Matrix pocket may initially impede flow and subsequently permit increased flow. In the short period following glaucoma surgery, it can be very important to avoid excessive outflow and maintain a minimal IOP. Failure to do this can result in hypotony and potentially serious complications. The C-Matrix pocket can be designed to serve as a liquid barrier in the short term following surgery. In an example construction, in the presence of liquid like water, an irrigating solution, or aqueous humor, the small fibers of the C-Matrix pocket can have the ability to resist liquid flow through the C-Matrix pocket. For example, with a relatively dense fiber matrix, due to the surface tension of the liquid, the C-Matrix pocket can initially resist penetration of the fluid into the volume of the C-Matrix pocket. Such a C-Matrix pocket can have the ability to hold an air reservoir (bubble) within the C-Matrix pocket, even though the C-Matrix pocket is not a closed body. As long as the fluid does not flow into the C-Matrix pocket, the C-Matrix pocket will act as a barrier to liquid flow (although some flow may occur around the C-Matrix pocket). As time passes, the air inside the C-Matrix pocket will naturally dissolve into the surrounding liquid, and liquid will take its place. At this stage flow will increase through the C-Matrix pocket.

In some embodiments, the pressure of the liquid against the C-Matrix pocket also can affect whether and how long the C-Matrix pocket acts as a barrier to flow. In the presence of a high pressure gradient, such as from large internal eye pressure, the surface tension will more easily break and fluid will flow more easily into the C-Matrix pocket volume. Thus, for patients with higher IOP, it may be desirable to select a C-Matrix pocket with a higher resistance to flow, such as a denser C-Matrix pocket.

In some embodiments, the property of changing states, from a barrier to a flow device, is closely related to the general characteristics of the C-Matrix pocket. These characteristics include: (1) fiber density (as the density increases, the pressure resistance increases), (2) type of material for the fibers (hydrophobic materials generally will hold a higher surface tension than hydrophilic materials), and (3) fiber thickness (for two materials with the same general porosity, as the fiber diameter becomes smaller, the C-Matrix pocket would hold a higher surface tension and higher pressure).

Figure 9:
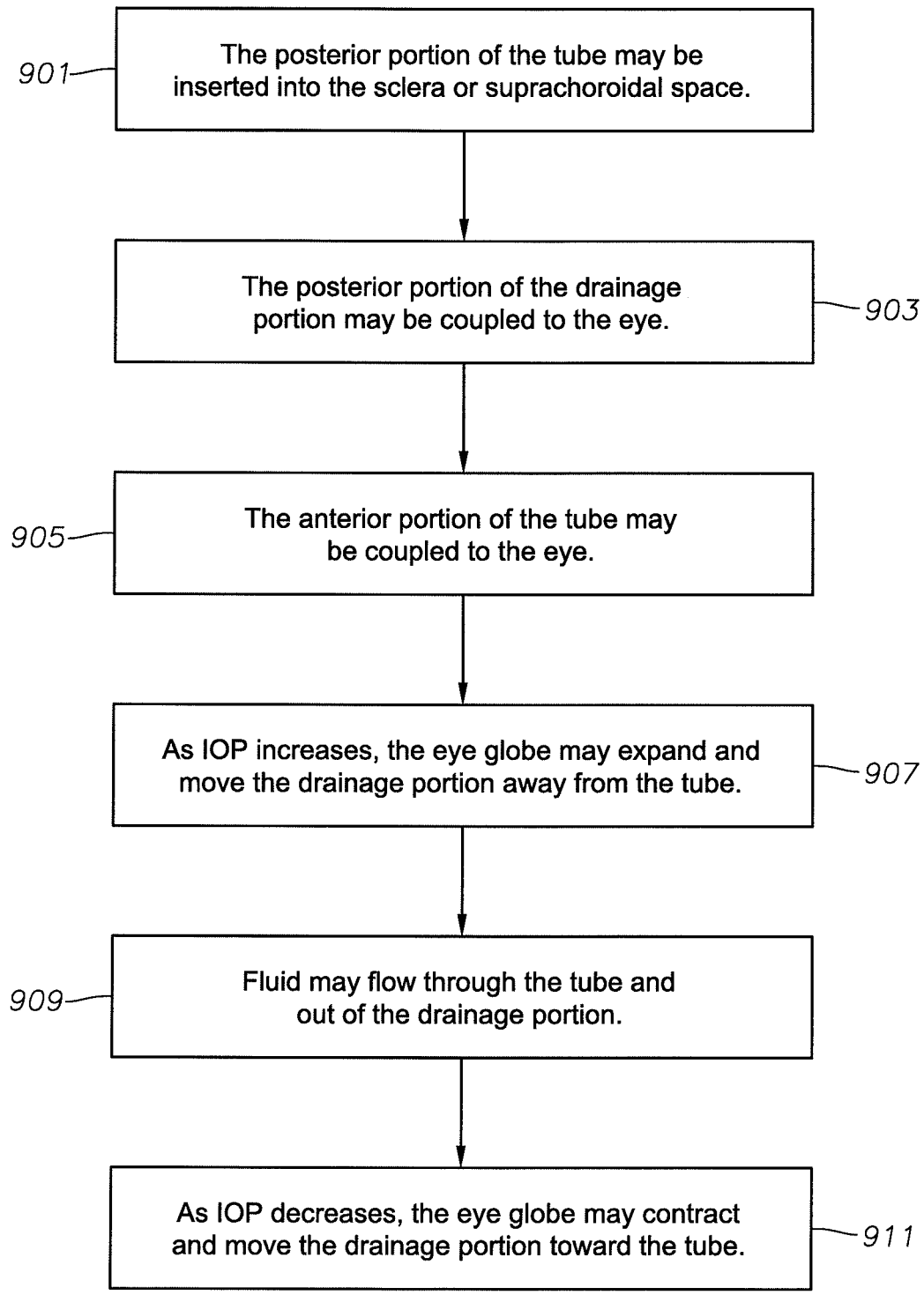
FIG. 9 illustrates a flowchart of a method for using the glaucoma shunt.

FIG. 9 illustrates a flowchart of a method for using the glaucoma shunt 200. The elements provided in the flowchart are illustrative only. Various provided elements may be omitted, additional elements may be added, and/or various elements may be performed in a different order than provided below.

At 901, the posterior portion of the tube 201 may be inserted into the sclera 190 or suprachoroidal space. In some embodiments, the tube 201 may include an anterior portion having an opening and a posterior portion. The tube may include a valve inside the tube that is coupled to a drainage portion 203.

At 903, the posterior portion of the drainage portion 203 may be coupled to the eye (e.g., through sutures 207a,b).

At 905, the anterior portion of the tube 201 may be coupled to the eye (e.g., sutured to a structure inside the eye's anterior chamber).

At 907, as IOP increases, the eye globe may expand and move the drainage portion 203 away from the tube 201. In some embodiments, the drainage portion 203 may be configured to move the valve relative to the tube 201 such that when the eye expands, the valve moves away from the opening to increase the size of the opening in the anterior portion of the tube. The larger opening allows for an increase in fluid flow through the opening.

At 909, fluid may flow through the tube 201 and out of the drainage portion 203.

At 911, as IOP decreases because of the fluid flow, the eye globe may contract and move the drainage portion 203 toward the tube 201. In some embodiments, the drainage portion 203 may be configured to move the valve relative to the tube 201 such that when the eye contracts, the valve moves toward the opening in the anterior portion of the tube 201 to decrease the size of the opening. The smaller opening reduces the fluid flow through the opening.

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A glaucoma shunt, comprising:
   a tube comprising an anterior portion having an opening and a posterior portion;
   a valve inside the tube;
   a drainage portion coupled to the valve;
   wherein the tube is configured to be coupled to a first portion of an eye;
   wherein the drainage portion is configured to be coupled to a second portion of the eye;
   wherein the drainage portion is configured to move the valve relative to the tube such that when the eye expands, the valve moves away from the opening in the anterior portion of the tube to increase fluid flow through the opening.

2. The glaucoma shunt of claim 1, wherein the drainage portion is further configured to move the valve relative to the tube such that when the eye contracts, the valve moves toward the opening in the anterior portion of the tube to decrease fluid flow through the opening.

3. The glaucoma shunt of claim 1, wherein the tube comprises suture holes for suturing the tube to the eye.

4. The glaucoma shunt of claim 1, wherein the drainage portion comprises suture holes for suturing the drainage portion to the eye.

5. The glaucoma shunt of claim 1, wherein the drainage portion comprises a C-Matrix.

6. The glaucoma shunt of claim 1, wherein the valve is arrow shaped.

7. The glaucoma shunt of claim 1, wherein the valve is coupled to the drainage portion through a flat back plate.

8. The glaucoma shunt of claim 1, wherein the drainage portion at least partially slides over the posterior portion of the tube.

9. The glaucoma shunt of claim 1, wherein the drainage portion is configured to initially resist fluid flow following implantation surgery and increase fluid flow after an air reservoir within the drainage portion dissolves.

10. A glaucoma shunt, comprising:
a tube comprising an anterior portion having an opening and a posterior portion;
an arrow-shaped valve inside the tube;
a C-Matrix pocket coupled to the valve;
wherein the tube is configured to be coupled to a first portion of an eye inside an anterior chamber of the eye;
wherein the drainage portion is configured to be coupled to a second portion of the eye in the sclera or suprachoroidal space;
wherein the C-Matrix pocket is configured to move the valve relative to the tube such that when the eye expands, the valve moves away from the opening in the anterior portion of the tube to increase a flow of aqueous humor through the opening.

11. The glaucoma shunt of claim 10, wherein the C-Matrix pocket is further configured to move the valve relative to the tube such that when the eye contracts, the valve moves toward the opening in the anterior portion of the tube to decrease a flow of aqueous humor through the opening.

12. The glaucoma shunt of claim 10, wherein the tube comprises suture holes for suturing the tube to the eye.

13. The glaucoma shunt of claim 10, wherein the C-Matrix pocket comprises suture holes for suturing the C-Matrix pocket to the eye.

14. The glaucoma shunt of claim 10, wherein the valve is coupled to the C-Matrix pocket through a flat back plate.

15. The glaucoma shunt of claim 10, wherein the C-Matrix pocket at least partially slides over the posterior portion of the tube.

16. The glaucoma shunt of claim 10, wherein the C-Matrix pocket is made of a nano fiber non-woven polymeric material.

17. The glaucoma shunt of claim 10, wherein the C-Matrix pocket is configured to initially resist fluid flow following implantation surgery and increase fluid flow after an air reservoir within the C-Matrix pocket dissolves.

* * * * *